United States Patent [19]
Cherpeck et al.

[11] Patent Number: 5,851,242
[45] Date of Patent: *Dec. 22, 1998

[54] FUEL ADDITIVE COMPOSITIONS CONTAINING POLYALKYLPHENOXY-AMINOALKANES AND POLY (OXYALKYLENE) AMINES

[75] Inventors: Richard E. Cherpeck, Cotati; Jack E. Morris, El Cerrito; Majid R. Ahmadi, Pinole, all of Calif.

[73] Assignee: Chevron Chemical Company, San Ramon, Calif.

[*] Notice: The term of this patent shall not extend beyond the expiration date of Pat. No. 5,669,939.

[21] Appl. No.: 846,717

[22] Filed: Apr. 30, 1997

Related U.S. Application Data

[63] Continuation-in-part of Ser. No. 645,992, May 14, 1996, Pat. No. 5,669,939.

[51] Int. Cl.$^6$ ....................................................... C10L 1/22
[52] U.S. Cl. ................ 44/425; 44/424; 44/433; 44/434; 44/387
[58] Field of Search .................................................. 44/425

[56] References Cited

U.S. PATENT DOCUMENTS

| | | | |
|---|---|---|---|
| 3,849,085 | 11/1974 | Kreuz et al. | 44/78 |
| 4,048,081 | 9/1977 | Machleder et al. | 252/51.5 R |
| 4,134,846 | 1/1979 | Machleder et al. | 252/51.5 A |
| 4,191,537 | 3/1980 | Lewis et al. | 44/71 |
| 4,247,301 | 1/1981 | Honnen | 44/63 |
| 4,259,086 | 3/1981 | Machleder et al. | 44/58 |
| 4,320,021 | 3/1982 | Lange | 252/51.5 R |
| 4,832,702 | 5/1989 | Kummer et al. | 44/62 |
| 4,881,945 | 11/1989 | Buckley, III | 44/72 |
| 5,112,364 | 5/1992 | Rath et al. | 44/418 |
| 5,669,939 | 9/1997 | Cherpeck | 44/425 |

FOREIGN PATENT DOCUMENTS

| | | | |
|---|---|---|---|
| 310875 | 4/1989 | European Pat. Off. | C10L 1/22 |
| 2105539 | 4/1972 | France | C07C 93/100 |

*Primary Examiner*—Ellen M. McAvoy
*Attorney, Agent, or Firm*—Claude J. Caroli

[57] ABSTRACT

A fuel additive composition comprising:
(a) a polyalkylphenoxyaminoalkane having the formula:

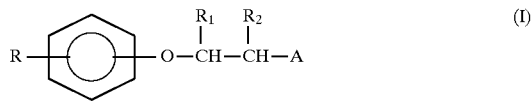

or a fuel soluble salt thereof, wherein R is a polyalkyl group having an average molecular weight in the range of about 600 to 5,000;

$R_1$ and $R_2$ are independently hydrogen or lower alkyl having 1 to 6 carbon atoms; and A is amino, N-alkyl amino having about 1 to about 20 carbon atoms in the alkyl group, N,N-dialkyl amino having about 1 to about 20 carbon atoms in each alkyl group, or a polyamine moiety having about 2 to about 12 amine nitrogen atoms and about 2 to about 40 carbon atoms; and (b) a poly(oxyalkylene) amine having at least one basic nitrogen atom and a sufficient number of oxyalkylene units to render the poly(oxyalkylene) amine soluble in hydrocarbons boiling in the gasoline or diesel fuel range.

The fuel additive compositions of this invention are useful as fuel additives for the prevention and control of engine deposits.

78 Claims, No Drawings

FUEL ADDITIVE COMPOSITIONS CONTAINING POLYALKYLPHENOXY-AMINOALKANES AND POLY(OXYALKYLENE) AMINES

This application is a continuation-in-part of application Ser. No. 08/645,992, filed May 14, 1996, now U.S. Pat. No. 5,669,939.

BACKGROUND OF THE INVENTION

1. Field of the Invention

This invention relates to fuel additive compositions containing polyalkylphenoxyaminoalkanes and poly(oxyalkylene) amines. In a further aspect, this invention relates to the use of these additive compositions in fuel compositions to prevent and control engine deposits.

2. Description of the Related Art

It is well known that automobile engines tend to form deposits on the surface of engine components, such as carburetor ports, throttle bodies, fuel injectors, intake ports and intake valves, due to the oxidation and polymerization of hydrocarbon fuel. These deposits, even when present in relatively minor amounts, often cause noticeable driveability problems, such as stalling and poor acceleration. Moreover, engine deposits can significantly increase an automobile's fuel consumption and production of exhaust pollutants. Therefore, the development of effective fuel detergents or "deposit control" additives to prevent or control such deposits is of considerable importance and numerous such materials are known in the art.

For example, aliphatic hydrocarbon-substituted phenols are known to reduce engine deposits when used in fuel compositions. U.S. Pat. No. 3,849,085, issued Nov. 19, 1974 to Kreuz et al., discloses a motor fuel composition comprising a mixture of hydrocarbons in the gasoline boiling range containing about 0.01 to 0.25 volume percent of a high molecular weight aliphatic hydrocarbon-substituted phenol in which the aliphatic hydrocarbon radical has an average molecular weight in the range of about 500 to 3,500. This patent teaches that gasoline compositions containing minor amounts of an aliphatic hydrocarbon-substituted phenol not only prevent or inhibit the formation of intake valve and port deposits in a gasoline engine, but also enhance the performance of the fuel composition in engines designed to operate at higher operating temperatures with a minimum of decomposition and deposit formation in the manifold of the engine.

U.S. Pat. No. 4,259,086, issued Mar. 31, 1981 to Machleder et al., discloses a detergent additive for fuels and lubricating oils which comprises the reaction product of an aliphatic hydrocarbon-substituted phenol, epichlorohydrin and a primary or secondary monoamine or polyamine. In addition, U.S. Pat. No. 4,048,081, issued Sep. 13, 1977 to Machleder et al., discloses a detergent additive for gasoline which is the reaction product of a polyisobutene phenol with epichlorohydrin, followed by amination with ethylene diamine or other polyamine.

Similarly, U.S. Pat. No. 4,134,846, issued Jan. 16, 1979 to Machleder et al., discloses a fuel additive composition comprising a mixture of (1) the reaction product of an aliphatic hydrocarbon-substituted phenol, epichlorohydrin and a primary or secondary mono- or polyamine, and (2) a polyalkylene phenol. This patent teaches that such compositions show excellent carburetor, induction system and combustion chamber detergency and, in addition, provide effective rust inhibition when used in hydrocarbon fuels at low concentrations.

Amino phenols are also known to function as detergents/dispersants, antioxidants and anti-corrosion agents when used in fuel compositions. U.S. Pat. No. 4,320,021, issued Mar. 16, 1982 to R. M. Lange, for example, discloses amino phenols having at least one substantially saturated hydrocarbon-based substituent of at least 30 carbon atoms. The amino phenols of this patent are taught to impart useful and desirable properties to oil-based lubricants and normally liquid fuels.

In addition, polybutylamines have been taught to be useful for preventing deposits in the intake system of internal combustion engines. For example, U.S. Pat. No. 4,832,702, issued May 23, 1989 to Kummer et al., discloses fuel and lubricant compositions containing polybutly or polyisobutylamine additives prepared by hydroformulating a polybutene or polyisobutene and then subjecting the resulting oxo product to a Mannich reaction or amination under hydrogenating conditions.

Polyether amine fuel additives are also well known in the art for the prevention and control of engine deposits. These polyether additives have a polyoxyalkylene "backbone", i.e., the polyether portion of the molecule consists of repeating oxyalkylene units. U.S. Pat. No. 4,191,537, issued Mar. 4, 1980 to Lewis et al., for example, discloses a fuel composition comprising a major portion of hydrocarbons boiling in the gasoline range and from 30 to 2,000 ppm of a hydrocarbyl polyoxyalkylene aminocarbamate having a molecular weight from about 600 to 10,000, and at least one basic nitrogen atom. The hydrocarbyl polyoxyalkylene moiety is composed of oxyalkylene units having from 2 to 5 carbon atoms in each oxyalkylene unit. These fuel compositions are taught to maintain the cleanliness of intake systems without contributing to combustion chamber deposits.

Aromatic compounds containing a poly(oxyalkylene) moiety are also known in the art. For example, the above-mentioned U.S. Pat. No. 4,191,537, discloses alkylphenyl poly(oxyalkylene) polymers which are useful as intermediates in the preparation of alkylphenyl poly(oxyalkylene) aminocarbamates.

Similarly, U.S. Pat. No. 4,881,945, issued Nov. 21, 1989 to Buckley, discloses a fuel composition comprising a hydrocarbon boiling in the gasoline or diesel range and from about 30 to about 5,000 parts per million of a fuel soluble alkylphenyl polyoxyalkylene aminocarbamate having at least one basic nitrogen and an average molecular weight of about 800 to 6,000 and wherein the alkyl group contains at least 40 carbon atoms.

U.S. Pat. No. 5,112,364, issued May 12, 1992 to Rath et al., discloses gasoline-engine fuels which contain small amounts of a polyetheramine and/or a polyetheramine derivative, wherein the polyetheramine is prepared by reductive amination of a phenol-initiated or alkylphenol-initiated polyether alcohol with ammonia or a primary amine.

U.S. Pat. No. 4,247,301, issued Jan. 27, 1981 to Honnen, discloses hydrocarbyl-substituted poly(oxyalkylene) polyamines, wherein the hydrocarbyl group contains from 1 to 30 carbon atoms and the polyamine moiety contains from 2 to 12 amine nitrogen atoms and from 2 to 40 carbon atoms. This patent teaches that the additives may be prepared by the reaction of a suitable hydrocarbyl-terminated polyether alcohol with a halogenating agent, such as HCl or thionyl chloride, to form a polyether chloride, followed by reaction of the polyether chloride with a polyamine to form the desired poly(oxyalkylene) polyamine. This patent also teaches at Example 6 that the polyether chloride may be reacted with ammonia or dimethylamine to form the corresponding polyether amine or polyether dimethylamine.

European Patent Application Publication No. 310,875, published Apr. 12, 1989 discloses fuels for spark ignition engines containing a polyetheramine additive prepared by first propoxylating and/or butoxylating an alkanol or primary or secondary alkylmonoamine and then aminating the resulting polyether with ammonia or a primary aliphatic amine.

French Patent No. 2,105,539, published Apr. 28, 1972, discloses carburetor detergent additives which are phenoxypropylamines which may be substituted with up to five hydrocarbon radicals of 1 to 30 carbon atoms on the aromatic ring. This patent also discloses additives obtained by reacting such phenoxypropylamines with alkylphosphoric acids.

Furthermore, commonly assigned copending U.S. patent application Ser. No. 08/645,992, filed May 14, 1996, discloses polyalkylphenoxyaminoalkanes and their use in fuel compositions for the prevention and control of engine deposits.

SUMMARY OF THE INVENTION

It has not been discovered that the combination of certain polyalkylphenoxyaminoalkanes with poly(oxyalkylene) amines provides excellent control of engine deposits, especially intake valve deposits, when employed as fuel additives in fuel compositions.

Accordingly, the present invention provides a novel fuel additive composition comprising:

(a) A polyalkylphenoxyaminoalkane compound having the following formula or a fuel soluble salt thereof:

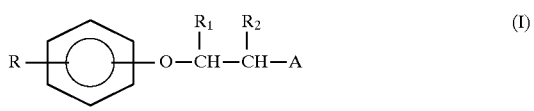

wherein R is a polyalkyl group having an average molecular weight in the range of about 600 to 5,000;

$R_1$ and $R_2$ are independently hydrogen or lower alkyl having 1 to 6 carbon atoms; and A is amino, N-alkyl amino having about 1 to about 20 carbon atoms in the alkyl group, N,N-dialkyl amino having about 1 to about 20 carbon atoms in each alkyl group, or a polyamine moiety having about 2 to about 12 amine nitrogen atoms and about 2 to about 40 carbon atoms; and (b) a poly(oxyalkylene) amine having at least one basic nitrogen atom and a sufficient number of oxyalkylene units to render the poly(oxyalkylene) amine soluble in hydrocarbons boiling in the gasoline or diesel fuel range.

The present invention further provides a fuel composition comprising a major amount of hydrocarbons boiling in the gasoline or diesel range and an effective deposit-controlling amount of the fuel additive composition of the present invention.

The present invention additionally provides a fuel concentrate comprising an inert stable oleophilic organic solvent boiling in the range of from about 150° F. to 400° F. and from about 10 to 70 weight percent of the fuel additive composition of the present invention.

Among other factors, the present invention is based on the surprising discovery that the unique combination of certain polyalkylphenoxyaminoalkanes with poly(oxyalkylene) amines provides excellent control of engine deposits, especially on intake valves, when employed as additives in fuel compositions.

DETAILED DESCRIPTION OF THE INVENTION

The Polyalkylphenoxyaminoalkane

The polyalkylphenoxyaminoalkane component of the present additive composition has the general formula:

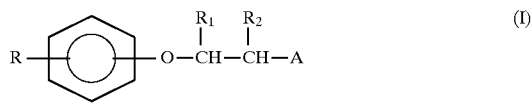

wherein R, $R_1$, $R_2$ and A are as defined above.

Preferably, R is a polyalkyl group having an average molecular weight in the range of about 600 to 3,000, more preferably about 700 to 3,000, and most preferably about 900 to 2,500.

Preferably, one of $R_1$ and $R_2$ is hydrogen or lower alkyl of 1 to 4 carbon atoms, and the other is hydrogen. More preferably, one of $R_1$ and $R_2$ is hydrogen, methyl or ethyl, and the other is hydrogen. Most preferably, $R_2$ is hydrogen, methyl or ethyl, and $R_1$ is hydrogen.

In general, A is amino, N-alkyl amino having from about 1 to about 20 carbon atoms in the alkyl group, preferably about 1 to about 6 carbon atoms, more preferably about 1 to about 4 carbon atoms; N,N-dialkyl amino having from about 1 to about 20 carbon atoms in each alkyl group, preferably about 1 to about 6 carbon atoms, more preferably about 1 to about 4 carbon atoms; or a polyamine moiety having from about 2 to about 12 amine nitrogen atoms and from about 2 to about 40 carbon atoms, preferably about 2 to 12 amine nitrogen atoms and about 2 to 24 carbon atoms. More preferably, A is amino or a polyamine moiety derived from a polyalkylene polyamine, including alkylene diamine. Most preferably, A is amino or a polyamine moiety derived from ethylene diamine or diethylene triamine.

It is preferred that the R substituent is located at the meta or, more preferably, the para position on the aromatic ring, i.e., para or meta relative to the ether group.

The compounds employed in the present invention will generally have a sufficient molecular weight so as to be non-volatile at normal engine intake valve operating temperatures (about 200°–250° C.). Typically, the molecular weight of the compounds employed in this invention will range from about 700 to about 3,500, preferably from about 700 to about 2,500.

Fuel-soluble salts of the compounds of formula I can be readily prepared for those compounds containing an amino or substituted amino group and such salts are contemplated to be useful for preventing or controlling engine deposits. Suitable salts include, for example, those obtained by protonating the amino moiety with a strong organic acid, such as an alkyl- or arylsulfonic acid. Preferred salts are derived from toluenesulfonic acid and methanesulfonic acid.

Definitions

As used herein, the following terms have the following meanings unless expressly stated to the contrary.

The term "amino" refers to the group: —$NH_2$.

The term "N-alkylamino" refers to the group: —$NHR_a$ wherein $R_a$ is an alkyl group. The term "N,N-dialkylamino" refers to the group: —$NR_bR_c$, wherein $R_b$ and $R_c$ are alkyl groups.

The term "hydrocarbyl" refers to an organic radical primarily composed of carbon and hydrogen which may be aliphatic, alicyclic, aromatic or combinations thereof, e.g., aralkyl or alkaryl. Such hydrocarbyl groups are generally free of aliphatic unsaturation, i.e., olefinic or acetylenic unsaturation, but may contain minor amounts of heteroatoms, such as oxygen or nitrogen, or halogens, such as chlorine.

The term "alkyl" refers to both straight- and branched-chain alkyl groups.

The term "lower alkyl" refers to alkyl groups having 1 to about 6 carbon atoms and includes primary, secondary and tertiary alkyl groups. Typical lower alkyl groups include, for example, methyl, ethyl, n-propyl, isopropyl, n-butyl, sec-butyl, t-butyl, n-pentyl, n-hexyl and the like.

The term "polyalkyl" refers to an alkyl group which is generally derived from polyolefins which are polymers or copolymers of mono-olefins, particularly 1-mono-olefins, such as ethylene, propylene, butylene, and the like. Preferably, the mono-olefin employed will have 2 to about 24 carbon atoms, and more preferably, about 3 to 12 carbon atoms. More preferred mono-olefins include propylene, butylene, particularly isobutylene, 1-octene and 1-decene. Polyolefins prepared from such mono-olefins include polypropylene, polybutene, especially polyisobutene, and the polyalphaolefins produced from 1-octene and 1-decene.

The term "fuel" or "hydrocarbon fuel" refers to normally liquid hydrocarbons having boiling points in the range of gasoline and diesel fuels.

General Synthetic Procedures

The polyalkylphenoxyaminoalkanes employed in this invention may be prepared by the following general methods and procedures. It should be appreciated that where typical or preferred process conditions (e.g., reaction temperatures, times, mole ratios of reactants, solvents, pressures, etc.) are given, other process conditions may also be used unless otherwise stated. Optimum reaction conditions may vary with the particular reactants or solvents used, but such conditions can be determined by one skilled in the art by routine optimization procedures.

Those skilled in the art will also recognize that it may be necessary to block or protect certain functional groups while conducting the following synthetic procedures. In such cases, the protecting group will serve to protect the functional group from undesired reactions or to block its undesired reaction with other functional groups or with the reagents used to carry out the desired chemical transformations. The proper choice of a protecting group for a particular functional group will be readily apparent to one skilled in the art. Various protecting groups and their introduction and removal are described, for example, in T. W. Greene and P. G. M. Wuts, *Protective Groups in Organic Synthesis*, Second Edition, Wiley, New York, 1991, and references cited therein.

Synthesis

The polyalkylphenoxyaminoalkanes employed in the present invention may be prepared by a process which initially involves hydroxyalkylation of a polyalkylphenol of the formula:

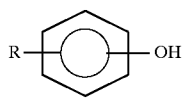

(II)

wherein R is as defined herein, with an alkylene carbonate of the formula:

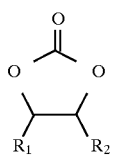

(III)

wherein $R_1$ and $R_2$ are as defined herein, in the presence of a catalytic amount of an alkali metal hydride or hydroxide, or alkali metal salt, to provide a polyalkylphenoxyalkanol of the formula:

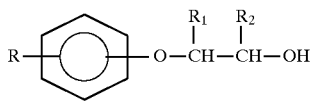

(IV)

wherein R, $R_1$ and $R_2$ are as defined herein.

The polyalkylphenols of formula II are well known materials and are typically prepared by the alkylation of phenol with the desired polyolefin or chlorinated polyolefin. A further discussion of polyalkylphenols can be found, for example, in U.S. Pat. No. 4,744,921 and U.S. Pat. No. 5,300,701.

Accordingly, the polyalkylphenols of formula II may be prepared from the corresponding olefins by conventional procedures. For example, the polyalkylphenols of formula II above may be prepared by reacting the appropriate olefin or olefin mixture with phenol in the presence of an alkylating catalyst at a temperature of from about 25° C. to 150° C., and preferably 30° C. to 100° C. either neat or in an essentially inert solvent at atmospheric pressure. A preferred alkylating catalyst is boron trifluoride. Molar ratios of reactants may be used. Alternatively, molar excesses of phenol can be employed, i.e., 2 to 3 equivalents of phenol for each equivalent of olefin with unreacted phenol recycled. The latter process maximizes monoalkylphenol. Examples of inert solvents include heptane, benzene, toluene, chlorobenzene and 250 thinner which is a mixture of aromatics, paraffins and naphthenes.

The polyalkyl substituent on the polyalkylphenols employed in the invention is generally derived from polyolefins which are polymers or copolymers of mono-olefins, particularly 1-mono-olefins, such as ethylene, propylene, butylene, and the like. Preferably, the mono-olefin employed will have 2 to about 24 carbon atoms, and more preferably, about 3 to 12 carbon atoms. More preferred mono-olefins include propylene, butylene, particularly isobutylene, 1-octene and 1-decene. Polyolefins prepared from such mono-olefins include polypropylene, polybutene, especially polyisobutene, and the polyalphaolefins produced from 1-octene and 1-decene.

The preferred polyisobutenes used to prepare the presently employed polyalkylphenols are polyisobutenes which comprise at least about 20% of the more reactive methylvinylidene isomer, preferably at least 50% and more preferably at least 70%. Suitable polyisobutenes include those prepared using $BF_3$ catalysts. The preparation of such polyisobutenes in which the methylvinylidene isomer comprises a high percentage of the total composition is described in U.S. Pat. Nos. 4,152,499 and 4,605,808. Such polyisobutenes, known as "reactive" polyisobutenes, yield high molecular weight alcohols in which the hydroxyl group is at or near the end of the hydrocarbon chain. Examples of suitable polyisobutenes having a high alkylvinylidene content include Ultravis 30, a polyisobutene having a number average molecular weight of about 1300 and a methylvinylidene content of about 74%, and Ultravis 10, a polyisobutene having a number average molecular weight of about 950 and a methylvinylidene content of about 76%, both available from British Petroleum.

The alkylene carbonates of formula III are known compounds which are available commercially or can be readily prepared using conventional procedures. Suitable alkylene carbonates include ethylene carbonate, propylene carbonate, 1,2-butylene carbonate, 2,3-butylene carbonate, and the like. A preferred alkylene carbonate is ethylene carbonate.

The catalyst employed in the reaction of the polyalkylphenol and alkylene carbonate may be any of the well known hydroxyalkylation catalysts. Typical hydroxyalkylation catalysts include alkali metal hydrides, such as lithium hydride, sodium hydride and potassium hydride, alkali metal hydroxides, such as sodium hydroxide and potassium hydroxide, and alkali metal salts, for example, alkali metal halides, such as sodium chloride and potassium chloride, and alkali metal carbonates, such as sodium carbonate and potassium carbonate. The amount of catalyst employed will generally range from about 0.01 to 1.0 equivalent, preferably from about 0.05 to 0.3 equivalent.

The polyalkylphenol and alkylene carbonate are generally reacted in essentially equivalent amounts in the presence of the hydroxyalkylation catalyst at a temperature in the range of about 100° C. to 210° C., and preferably from about 150° C. to about 170° C. The reaction may take place in the presence or absence of an inert solvent.

The time of reaction will vary depending on the particular alkylphenol and alkylene carbonate reactants, the catalyst used and the reaction temperature. Generally, the reaction time will range from about two hours to about five hours. The progress of the reaction is typically monitored by the evolution of carbon dioxide. At the completion of the reaction, the polyalkylphenoxyalkanol product is isolated using conventional techniques.

The hydroxyalkylation reaction of phenols with alkylene carbonates is well known in the art and is described, for example, in U.S. Pat. Nos. 2,987,555; 2,967,892; 3,283,030 and 4,341,905.

Alternatively, the polyalkylphenoxyalkanol product of formula IV may be prepared by reacting the polyalkylphenol of formula II with an alkylene oxide of the formula:

wherein $R_1$ and $R_2$ are as defined herein, in the presence of a hydroxyalkylation catalyst as described above.

Suitable alkylene oxides of formula V include ethylene oxide, propylene oxide, 1,2-butylene oxide, 2,3-butylene oxide, and the like. A preferred alkylene oxide is ethylene oxide.

In a manner similar to the reaction with alkylene carbonate, the polyalkylphenol and alkylene oxide are reacted in rr essentially equivalent or equimolar amounts in the presence of 0.01 to 1.0 equivalent of a hydroxyalkylation catalyst, such as sodium or potassium hydride, at a temperature in the range of about 30° C. to about 150° C., for about 2 to about 24 hours. The reaction may be conducted in the presence or absence of a substantially anhydrous inert solvent. Suitable solvents include toluene, xylene, and the like. Generally, the reaction is conducted at a pressure sufficient to contain the reactants and any solvent present, typically at atmospheric or higher pressure. Upon completion of the reaction, the polyalkylphenoxyalkanol is isolated by conventional procedures.

The polyalkylphenoxyalkanol of formula IV is subsequently reacted, either directly or through an intermediate, with an appropriate amine to provide the desired polyalkylphenoxyaminoalkanes of formula I. Suitable amine reactants which may be employed to form the amine component, i.e., substituent A, of the polyalkylphenoxyaminoalkanes employed in the present invention are discussed more fully below.

The Amine Component of the Polyalkylphenoxyaminoalkane

In general, the amine component of the presently employed polyalkylphenoxyaminoalkanes will contain an average of at least about one basic nitrogen atom per molecule. A "basic nitrogen atom" is one that is titratable by a strong acid, for example, a primary, secondary, or tertiary amine nitrogen; as distinguished from, for example, an carbamyl nitrogen, e.g., —OC(O)NH—, which is not titratable with a strong acid. Preferably, at least one of the basic nitrogen atoms of the amine component will be primary or secondary amine nitrogen, more preferably, at least one will be a primary amine nitrogen.

The amine component of the polyalkylphenoxyaminoalkanes employed in this invention is preferably derived from ammonia, a primary alkyl or secondary dialkyl monoamine, or a polyamine having a terminal amino nitrogen atom.

Primary alkyl monoamines useful in preparing compounds employed in the present invention contain 1 nitrogen atom and from about 1 to about 20 carbon atoms, more preferably about 1 to 6 carbon atoms, most preferably 1 to 4 carbon atoms. Examples of suitable monoamines include N-methylamine, N-ethylamine, N-n-propylamine, N-isopropylamine, N-n-butylamine, N-isobutylamine, N-sec-butylamine, N-tert-butylamine, N-n-pentylamine, N-cyclopentylamine, N-n-hexylamine, N-cyclohexylamine, N-octylamine, N-decylamine, N-dodecylamine, N-octadecylamine, N-benzylamine, N-(2-phenylethyl) amine, 2-aminoethanol, 3-amino-1-propanol, 2-(2-aminoethoxy)ethanol, N-(2-methoxyethyl)amine, N-(2-ethoxyethyl)amine and the like. Preferred primary amines are N-methylamine, N-ethylamine and N-n-propylamine.

The amine component of the presently employed polyalkylphenoxyaminoalkanes may also be derived from a secondary dialkyl monoamine. The alkyl groups of the secondary amine may be the same or different and will generally each contain about 1 to about 20 carbon atoms, more preferably about 1 to about 6 carbon atoms, most preferably about 1 to about 4 carbon atoms. One or both of the alkyl groups may also contain one or more oxygen atoms.

Preferably, the alkyl groups of the secondary amine are independently selected from the group consisting of methyl, ethyl, propyl, butyl, pentyl, hexyl, 2-hydroxyethyl and 2-methoxyethyl. More preferably, the alkyl groups are methyl, ethyl or propyl.

Typical secondary amines which may be used in this invention include N,N-dimethylamine, N,N-diethylamine, N,N-di-n-propylamine, N,N-diisopropylamine, N,N-di-n-butylamine, N,N-di-sec-butylamine, N,N-di-n-pentylamine, N,N-di-n-hexylamine, N,N-dicyclohexylamine, N,N-dioctylamine, N-ethyl-N-methylamine, N-methyl-N-n-propylamine, N-n-butyl-N-methylamine, N-methyl-N-octylamine, N-ethyl-N-isopropylamine, N-ethyl-N-octylamine, N,N-di(2-hydroxyethyl)amine, N,N-di(3-hydroxypropyl)amine, N,N-di(ethoxyethyl)amine, N,N-di (propoxyethyl)amine and the like. Preferred secondary amines are N,N-dimethylamine, N,N-diethylamine and N,N-di-n-propylamine.

Cyclic secondary amines may also be employed to form the additives employed in this invention. In such cyclic compounds, the alkyl groups, when taken together, form one or more 5- or 6-membered rings containing up to about 20 carbon atoms. The ring containing the amine nitrogen atom is generally saturated, but may be fused to one or more saturated or unsaturated rings. The rings may be substituted with hydrocarbyl groups of from 1 to about 10 carbon atoms and may contain one or more oxygen atoms.

Suitable cyclic secondary amines include piperidine, 4-methylpiperidine, pyrrolidine, morpholine, 2,6-dimethylmorpholine and the like.

Suitable polyamines can have a straight- or branched-chain structure and may be cyclic or acyclic or combinations thereof. Generally, the amine nitrogen atoms of such polyamines will be separated from one another by at least two carbon atoms, i.e., polyamines having an aminal structure are not suitable. The polyamine may also contain one or more oxygen atoms, typically present as an ether or a hydroxyl group. Polyamines having a carbon-to-nitrogen ratio of from about 1:1 to about 10:1 are particularly preferred.

In preparing polyalkylphenoxyaminoalkane compounds using a polyamine where the various nitrogen atoms of the polyamine are not geometrically equivalent, several substitutional isomers are possible and each of these possible isomers is encompassed within this invention.

A particularly preferred group of polyamines for use in the present invention are polyalkylene polyamines, including alkylene diamines. Such polyalkylene polyamines will typically contain from about 2 to about 12 nitrogen atoms and from about 2 to about 40 carbon atoms, preferably about 2 to 24 carbon atoms. Preferably, the alkylene groups of such polyalkylene polyamines will contain from about 2 to about 6 carbon atoms, more preferably from about 2 to about 4 carbon atoms.

Examples of suitable polyalkylene polyamines include ethylenediamine, propylenediamine, isopropylenediamine, butylenediamine, pentylenediamine, hexylenediamine, diethylenetriamine, dipropylenetriamine, dimethylaminopropylamine, diisopropylenetriamine, dibutylenetriamine, di-sec-butylenetriamine, triethylenetetraamine, tripropylenetetraamine, triisobutylenetetraamine, tetraethylenepentamine, pentaethylenehexamine, dimethylaminopropylamine, and mixtures thereof.

Particularly suitable polyalkylene polyamines are those having the formula:

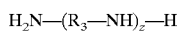

wherein $R_3$ is a straight- or branched-chain alkylene group having from about 2 to about 6 carbon atoms, preferably from about 2 to about 4 carbon atoms, most preferably about 2 carbon atoms, i.e., ethylene ($—CH_2CH_2—$); and z is an integer from about 1 to about 4, preferably about 1 or about 2.

Particularly preferred polyalkylene polyamines are ethylenediamine, diethylenetriamine, triethylenetetraamine, and tetraethylenepentamine. Most preferred are ethylenediamine and diethylenetriamine, especially ethylenediamine.

Also contemplated for use in the present invention are cyclic polyamines having one or more 5- to 6-membered rings. Such cyclic polyamines compounds include piperazine, 2-methylpiperazine, N-(2-aminoethyl) piperazine, N-(2-hydroxyethyl)piperazine, 1,2-bis-(N-piperazinyl) ethane, 3-aminopyrrolidine, N-(2-aminoethyl) pyrrolidine, and the like. Among the cyclic polyamines, the piperazines are preferred.

Many of the polyamines suitable for use in the present invention are commercially available and others may be prepared by methods which are well known in the art. For example, methods for preparing amines and their reactions are detailed in Sidgewick's "The Organic Chemistry of Nitrogen", Clarendon Press, Oxford, 1966; Noller's "Chemistry of Organic Compounds", Saunders, Philadelphia, 2nd Ed., 1957; and Kirk-Othmer's "Encyclopedia of Chemical Technology", 2nd Ed., especially Volume 2, pp. 99–116.

Preparation of the Polyalkylphenoxyaminoalkane

As noted above, the polyalkylphenoxyaminoalkanes employed in the present invention may be conveniently prepared by reacting the polyalkylphenoxyalkanol of formula IV, either directly or through an intermediate, with a nitrogen-containing compound, such as ammonia, a primary or secondary alkyl monoamine, or a polyamine, as described herein.

Accordingly, the polyalkylphenoxyalkanol of formula IV may be converted to the desired polyalkylphenoxyaminoalkane by a variety of procedures known in the art.

For example, the terminal hydroxy group on the polyalkylphenoxyalkanol may first be converted to a suitable leaving group, such as a mesylate, chloride or bromide, and the like, by reaction with a suitable reagent, such as methanesulfonyl chloride. The resulting polyalkylphenoxyalkyl mesylate or equivalent intermediate may then be converted to a phthalimide derivative by reaction with potassium phthalimide in the presence of a suitable solvent, such as N,N-dimethylforamide. The polyalkylphenoxyalkyl phthalimide derivative is subsequently converted to the desired polyalkylphenoxyaminoalkane by reaction with a suitable amine, such as hydrazine. Alternatively, the leaving group can be converted to an azide, as described, for example, in Turnbull Scriven, Chemical Reviews, Volume 88, pages 297–368, 1988. The azide is subsequently converted to the desired polyalkylphenoxyaminoalkane by reduction with hydrogen and a catalyst, such as palladium on carbon or a Lindlar catalyst.

The polyalkylphenoxyalkanol of formula IV may also be converted to the corresponding polyyalkylphenoxyalkyl chloride by reaction with a suitable halogenating agent, such as HCl, thionyl chloride, or epichlorohydrin, followed by displacement of the chloride with a suitable amine, such as ammonia, a primary or secondary alkyl monoamine, or a polyamine, as described, for example, in U.S. Pat. No. 4,247,301 to Honnen, the disclosure of which is incorporated herein by reference.

Alternatively, the polyalkylphenoxyaminoalkanes employed in the present invention may be prepared from the corresponding polyalkylphenoxyalkanol by a process commonly referred to as reductive amination, such as described in U.S. Pat. No. 5,112,364 to Rath et al. and U.S. Pat. No. 4,332,595 to Herbstman et al., the disclosures of which are incorporated herein by reference.

In the reductive amination procedure, the polyalkylphenoxyalkanol is aminated with an appropriate amine, such as ammonia or a primary alkyl monoamine, in the presence of hydrogen and a hydrogenation-dehydrogenation catalyst. The amination reaction is typically carried out at temperatures in the range of about 160° C. to about 250° C. and pressures of about 1,000 to about 5,000 psig, preferably about 1,500 to about 3,000 psig. Suitable hydrogenation-dehydrogenation catalysts include those containing platinum, palladium, cobalt, nickel, copper, or chromium, or mixtures thereof. Generally, an excess of the ammonia or amine reactant is used, such as about a 5-fold to about 60-fold molar excess, and preferably about a 10-fold to about 40-fold molar excess, of ammonia or amine.

When the reductive amination is carried out with a polyamine reactant, the amination is preferably conducted using a two-step procedure as described in commonly-assigned copending U.S. patent application Ser. No. 08/574,485, filed Dec. 19, 1995, and titled, "Reductive Amination Process for Manufacturing a Fuel Additive From Polyoxybutylene Alcohol with Ethylene Diamine", the disclosure of which is incorporated herein by reference in its entirety. According to this procedure, an appropriate alcohol is first contacted with a hydrogenation-dehydrogenation catalyst at a temperature of at least 230° C. to provide a carbonyl-containing intermediate, which is subsequently reacted with a polyamine at a temperature below about 190° C. in the presence of hydrogen and a hydrogenation catalyst to produce the desired polyamine adduct.

In an alternative procedure for preparing the polyalkylphenoxyaminoalkanes employed in the present invention, the polyalkylphenol of formula II may be reacted with an aziridine of the formula:

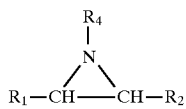
(VI)

wherein $R_1$ and $R_2$ are as defined herein, and $R_4$ is hydrogen or alkyl of 1 to 20 carbon atoms. A preferred aziridine is one wherein $R_1$ is hydrogen, $R_2$ is hydrogen, methyl or ethyl, and $R_4$ is hydrogen.

The reaction of aziridines with alcohols to produce beta-amino ethers is well known in the art and is discussed, for example, in Ham and Dermer, "Ethyleneimine and Other Aziridines", Academic Press, New York, 1969, pages 224–227 and 256–257.

The Poly(oxyalkylene) Amine

The poly(oxyalkylene) amine component of the present fuel additive composition is a poly(oxyalkylene) amine having at least one basic nitrogen atom and a sufficient number of oxyalkylene units to render the poly(oxyalkylene) amine soluble in hydrocarbons boiling in the gasoline or diesel range.

Preferably, such poly(oxyalkylene) amines will also be of sufficient molecular weight so as to be nonvolatile at normal engine intake valve operating temperatures, which are generally in the range of about 200° C. to 250° C.

Generally, the poly(oxyalkylene) amines suitable for use in the present invention will contain at least about 5 oxyalkylene units, preferably about 5 to 100, more preferably about 8 to 100, and even more preferably about 10 to 100. Especially preferred poly(oxyalkylene) amines will contain about 10 to 25 oxyalkylene units.

The molecular weight of the presently employed poly(oxyalkylene) amines will generally range from about 500 to about 10,000, preferably from about 500 to about 5,000.

Suitable poly(oxyalkylene) amine compounds for use in the present invention include hydrocarbyl poly(oxyalkylene) polyamines as disclosed, for example, in U.S. Pat. No. 4,247,301, issued Jan. 27, 1981 to Honnen, the disclosure of which is incorporated herein by reference. These compounds are hydrocarbyl poly(oxyalkylene) polyamines wherein the poly(oxyalkylene) moiety comprises at least one hydrocarbyl-terminated poly(oxyalkylene) chain of 2 to 5 carbon atom oxyalkylene units, and wherein the poly (oxyalkylene) chain is bonded through a terminal carbon atom to a nitrogen atom of a polyamine having from 2 to about 12 amine nitrogen atoms and from 2 to about 40 carbon atoms with a carbon-to-nitrogen ratio between about 1:1 and 10:1. The hydrocarbyl group on these hydrocarbyl poly(oxyalkylene) polyamines will contain from about 1 to 30 carbon atoms. These compounds generally have molecular weights in the range of about 500 to 10,000, preferably from about 500 to 5,000 and more preferably from about 800 to 5,000.

The above-described hydrocarbyl poly(oxyalkylene) polyamines are prepared by conventional procedures known in the art, as taught, for example, in U.S. Pat. No. 4,247,301.

Other poly(oxyalkylene) amines suitable for use in the present invention are the poly(oxyalkylene) polyamines wherein the poly(oxyalkylene) moiety is connected to the polyamine moiety through an oxyalkylene hydroxy-type linkage derived from an epihalohydrin, such as epichlorohydrin or epibromohydrin. This type of poly(oxyalkylene) amine having an epihalohydrin-derived linkage is described, for example, in U.S. Pat. No. 4,261,704, issued Apr. 14, 1981 to Langdon, the disclosure of which is incorporated herein by reference.

Useful polyamines for preparing the epihalohydrin-derived poly(oxyalkylene) polyamines include, for example, alkylene polyamines, polyalkylene polyamines, cyclic amines, such as piperazines, and amino-substituted amines. The poly(oxyalkylene) polyamines having an epihalohydrin-derived linkage between the poly (oxyalkylene) and polyamine moieties are prepared using known procedures as taught, for example, in U.S. Pat. No. 4,261,704.

Another type of poly(oxyalkylene) amine useful in the present invention is a highly branched alkyl poly (oxyalkylene) monoamine as described, for example in U.S. Pat. No. 5,094,667, issued Mar. 10, 1992 to Schilowitz et al., the disclosure of which is incorporated herein by reference. These highly branched alkyl poly(oxyalkylene) monoamines have the general formula:

(VII)

wherein $R_4$ is a highly branched alkyl group containing from 12 to 40 carbon atoms, preferably an alkyl group having 20 carbon atoms which is derived from a Guerbet condensation reaction, and p is a number up to 30, preferably 4 to 8. The preferred alkyl group is derived from a Guerbet alcohol containing 20 carbon atoms having the formula:

(VIII)

wherein $R_5$ is a hydrocarbyl chain.

The above highly branched alkyl poly(oxyalkylene) monoamines are prepared by using known methods as disclosed, for example, in U.S. Pat. No. 5,094,667.

A preferred class of poly(oxyalkylene) amine for use in the fuel additive composition of the present invention are hydrocarbyl poly(oxyalkylene) monoamines as described, for example, in U.S. Pat. No. 5,112,364, issued May 12, 1992 to Rath et al., the disclosure of which is incorporated herein by reference. As disclosed in U.S. Pat. No. 5,112,364, such poly(oxyalkylene) monoamines may be prepared by the reductive amination of a phenol-initiated or alkylphenol-initiated poly(oxyalkylene) alcohol with ammonia or a primary amine.

In addition, the above-mentioned U.S. Pat. No. 4,247,301 to Honnen discloses hydrocarbyl poly(oxyalkylene) monoamines which are suitable for use in the present fuel additive composition. In particular, Example 6 of this patent describes alkylphenyl poly(oxyalkylene) monoamines prepared from ammonia and dimethylamine.

A particularly preferred type of hydrocarbyl poly (oxyalkylene) monoamine is an alkylphenyl poly (oxyalkylene) monoamine wherein the poly(oxyalkylene)

moiety contains oxypropylene units or oxybutylene units or mixtures of oxypropylene and oxybutylene units. Preferably, the alkyl group on the alkylphenyl moiety is a straight or branched-chain alkyl of 1 to 24 carbon atoms. An especially preferred alkylphenyl moiety is tetrapropenylphenyl, that is, where the alkyl group is a branched-chain alkyl of 12 carbon atoms derived from propylene tetramer.

A further discussion of the hydrocarbon-substituted poly(oxyalkylene) moiety on the poly(oxyalkylene) amine component of the present fuel additive composition is found hereinbelow.

Another preferred class of poly(oxyalkylene) amine for use in the fuel additive composition of the present invention are hydrocarbyl-substituted poly(oxyalkylene) aminocarbamates disclosed, for example, in U.S. Pat. Nos. 4,288,612; 4,236,020; 4,160,648; 4,191,537; 4,270,930; 4,233,168; 4,197,409; 4,243,798 and 4,881,945, the disclosure of each of which are incorporated herein by reference.

These hydrocarbyl poly(oxyalkylene) aminocarbamates contain at least one basic nitrogen atom and have an average molecular weight of about 500 to 10,000, preferably about 500 to 5,000, and more preferably about 1,000 to 3,000. As described more fully hereinbelow, these hydrocarbyl poly(oxyalkylene) aminocarbamates contain (a) a poly(oxyalkylene) moiety, (b) an amine moiety and (c) a carbamate connecting group.

A. The Poly(oxyalkylene) Moiety

The hydrocarbyl-terminated poly(oxyalkylene) polymers which are utilized in preparing the hydrocarbyl poly(oxyalkylene) aminocarbamates employed in the present invention are monohydroxy compounds, e.g., alcohols, often termed monohydroxy polyethers, or polyalkylene glycol monocarbyl ethers, or "capped" poly(oxyalkylene) glycols, and are to be distinguished from the poly(oxyalkylene) glycols (diols), or polyols, which are not hydrocarbyl-terminated, i.e., are not capped. These hydrocarbyl poly(oxyalkylene) alcohols may be produced by the addition of lower alkylene oxides, such as ethylene oxide, propylene oxide, butylene oxide, etc. to a hydroxy compound, $R_9OH$, under polymerization conditions, wherein $R_9$ is the hydrocarbyl group which caps the poly(oxyalkylene) chain.

In the hydrocarbyl poly(oxyalkylene) aminocarbamates employed in the present invention, the hydrocarbyl group $R_9$ will generally contain from 1 to about 30 carbon atoms, preferably from 2 to about 20 carbon atoms and is preferably aliphatic or aromatic, i.e., an alkyl or alkyl phenyl wherein the alkyl is a straight or branched-chain of from 1 to about 24 carbon atoms. More preferably, $R_9$ is alkylphenyl wherein the alkyl group is a branched-chain of 12 carbon atoms, derived from propylene tetramer, and commonly referred to as tetrapropenyl.

The oxyalkylene units in the poly(oxyalkylene) moiety preferably contain from 2 to about 5 carbon atoms but one or more units of a larger carbon number may also be present. Generally, each poly(oxyalkylene) polymer contains at least about 5 oxyalkylene units, preferably about 5 to about 100 oxyalkylene units, more preferably about 8 to about 100 units, even more preferably about 10 to 100 units, and most preferably 10 to about 25 such units. The poly(oxyalkylene) moiety of the hydrocarbyl poly(oxyalkylene) aminocarbamates employed in the present invention is more fully described and exemplified in U.S. Pat. No. 4,191,537, issued Mar. 4, 1980 to Lewis, the disclosure of which is incorporated herein by reference.

Although the hydrocarbyl group on the hydrocarbyl poly(oxyalkylene) moiety will preferably contain from 1 to about 30 carbon atoms, longer hydrocarbyl groups, particularly longer chain alkyl phenyl groups, may also be employed. For example, alkylphenyl poly(oxyalkylene) aminocarbamates wherein the alkyl group contains at least 40 carbon atoms, as described in U.S. Pat. No. 4,881,945, issued Nov. 21, 1989 to Buckley, are also contemplated for use in the present invention. The alkyl phenyl group on the aminocarbamates of U.S. Pat. No. 4,881,945 will preferably contain an alkyl group of 50 to 200 carbon atoms, and more preferably, an alkyl group of 60 to 100 carbon atoms. These longer chain alkyl groups will generally be derived from olefin polymers, such as polybutene. The disclosure of U.S. Pat. No. 4,881,945 is incorporated herein by reference.

Also contemplated for use in the present invention are alkylphenyl poly(oxypropylene) aminocarbamates wherein the alkyl group is a substantially straight-chain alkyl group of about 25 to 50 carbon atoms derived from an alpha olefin oligomer of $C_8$ to $C_{20}$ alpha olefins, as described in PCT International Patent Application Publication No. WO 90/07564, published Jul. 12, 1990, the disclosure of which is incorporated herein by reference.

B. The Amine Moiety

The amine moiety of the hydrocarbyl poly(oxyalkylene) aminocarbamate is preferably derived from a polyamine having from 2 to about 12 amine nitrogen atoms and from 2 to about 40 carbon atoms.

The polyamine is preferably reacted with a hydrocarbyl poly(oxyalkylene) chloroformate to produce the hydrocarbyl poly(oxyalkylene) aminocarbamate fuel additive finding use within the scope of the present invention. The chloroformate is itself derived from the hydrocarbyl poly(oxyalkylene) alcohol by reaction with phosgene.

The polyamine provides the hydrocarbyl poly(oxyalkylene) aminocarbamate with, on the average, at least about one basic nitrogen atom per carbamate molecule, i.e., a nitrogen atom titratable by strong acid. The polyamine preferably has a carbon-to-nitrogen ratio of from about 1:1 to about 10:1. The polyamine may be substituted with substituents selected from hydrogen, hydrocarbyl groups of from 1 to about 10 carbon atoms, acyl groups of from 2 to about 10 carbon atoms, and monoketone, monohydroxy, mononitro, monocyano, alkyl and alkoxy derivatives of hydrocarbyl groups of from 1 to 10 carbon atoms. It is preferred that at least one of the basic nitrogen atoms of the polyamine is a primary or secondary amino nitrogen. The amine moiety of the hydrocarbyl poly(oxyalkylene) aminocarbamates employed in the present invention has been described and exemplified more fully in U.S. Pat. No. 4,191,537.

A more preferred polyamine for use in preparing the hydrocarbyl poly(oxyalkylene) aminocarbamates finding use within the scope of the present invention is a polyalkylene polyamine, including alkylenediamine, and including substituted polyamines, e.g., alkyl and hydroxyalkyl-substituted polyalkylene polyamine. Preferably, the alkylene group contains from 2 to 6 carbon atoms, there being preferably from 2 to 3 carbon atoms between the nitrogen atoms. Examples of such polyamines include ethylenediamine, diethylenetriamine, triethylenetetramine, di(trimethylene)triamine, dipropylenetriamine, tetraethylenepentamine, etc.

Among the polyalkylene polyamines, polyethylene polyamine and polypropylene polyamine containing 2 to about 12 amine nitrogen atoms and 2 to about 24 carbon atoms are especially preferred and in particular, the lower polyalkylene polyamines, e.g., ethylenediamine, diethylenetriamine, propylenediamine, dipropylenetriamine, etc., are most preferred.

C. The Aminocarbamate Connecting Group

The hydrocarbyl poly(oxyalkylene) aminocarbamate employed as the poly(oxyalkylene) amine component of the fuel additive composition of the present invention is obtained by linking the polyamine and the hydrocarbyl poly(oxyalkylene) alcohol together through a carbamate linkage, i.e.,

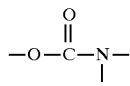

wherein the oxygen may be regarded as the terminal hydroxyl oxygen of the poly(oxyalkylene) alcohol, the nitrogen is derived from the polyamine and the carbonyl group —C(O)—, is preferably provided by a coupling agent, such as phosgene.

In a preferred method of preparation, the hydrocarbyl poly(oxyalkylene) alcohol is reacted with phosgene to produce a chloroformate and the chloroformate is reacted with the polyamine. Since there may be more than one nitrogen atom of the polyamine which is capable of reacting with the chloroformate, the carbamate product may contain more than one hydrocarbyl poly(oxyalkylene) moiety. It is preferred that the hydrocarbyl poly(oxyalkylene) aminocarbamate product contains on the average, about one poly(oxyalkylene) moiety per molecule (i.e., is a monocarbamate), although it is understood that this reaction route may lead to mixtures containing appreciable amounts of di- or higher poly(oxyalkylene) chain substitution on a polyamine containing several reactive nitrogen atoms.

A particularly preferred aminocarbamate is alkylphenyl poly(oxybutylene) aminocarbamate, wherein the amine moiety is derived from ethylene diamine or diethylene triamine. Synthetic methods to avoid higher degrees of substitution, methods of preparation, and other characteristics of the aminocarbamates used in the present invention are more fully described and exemplified in U.S. Pat. No. 4,191,537.

Fuel Compositions

The fuel additive composition of the present invention will generally be employed in hydrocarbon fuels to prevent and control engine deposits, particularly intake valve deposits. The proper concentration of additive necessary to achieve the desired deposit control varies depending upon the type of fuel employed, the type of engine, and the presence of other fuel additives.

Generally, the present fuel additive composition will be employed in a hydrocarbon fuel in a concentration ranging from about 50 to about 5,000 parts per million (ppm) by weight, preferably from 100 to 2,500 ppm.

In terms of individual components, hydrocarbon fuel containing the fuel additive composition of this invention will generally contain about 25 to 2,000 ppm of the polyalkylphenoxyaminoalkane component and about 25 to 2,000 ppm of the poly(oxyalkylene) amine component. The ratio of the polyalkylphenoxyaminoalkane to poly(oxyalkylene) amine will generally range from about 0.05:1 to about 5:1, and will preferably be about 2:1 or less.

The fuel additive composition of the present invention may be formulated as a concentrate using an inert stable oleophilic (i.e., dissolves in gasoline) organic solvent boiling in the range of about 150° F. to 400° F. (about 65° C. to 205° C.). Preferably, an aliphatic or an aromatic hydrocarbon solvent is used, such as benzene, toluene, xylene or higher-boiling aromatics or aromatic thinners. Aliphatic alcohols containing about 3 to 8 carbon atoms, such as isopropanol, isobutylcarbinol, n-butanol and the like, in combination with hydrocarbon solvents are also suitable for use with the present additives. In the concentrate, the amount of the additive will generally range from about 10 to about 70 weight percent, preferably 10 to 50 weight percent, more preferably from 20 to 40 weight percent.

In gasoline fuels, other fuel additives may be employed with the additive composition of the present invention, including, for example, oxygenates, such as t-butyl methyl ether, antiknock agents, such as methylcyclopentadienyl manganese tricarbonyl, and other dispersants/detergents, such as hydrocarbyl amines, or succinimides. Additionally, antioxidants, metal deactivators, demulsifiers and carburetor or fuel injector detergents may be present.

In diesel fuels, other well-known additives can be employed, such as pour point depressants, flow improvers, cetane improvers, and the like.

A fuel-soluble, nonvolatile carrier fluid or oil may also be used with the fuel additive composition of this invention. The carrier fluid is a chemically inert hydrocarbon-soluble liquid vehicle which substantially increases the nonvolatile residue (NVR), or solvent-free liquid fraction of the fuel additive composition while not overwhelmingly contributing to octane requirement increase. The carrier fluid may be a natural or synthetic fluid, such as mineral oil, refined petroleum oils, synthetic polyalkanes and alkenes, including hydrogenated and unhydrogenated polyalphaolefins, and synthetic polyoxyalkylene-derived fluids, such as those described, for example, in U.S. Pat. No. 4,191,537 to Lewis, and polyesters, such as those described, for example, in U.S. Pat. Nos. 3,756,793 to Robinson and 5,004,478 to Vogel et al., and in European Patent Application Nos. 356,726, published Mar. 7, 1990, and 382,159, published Aug. 16, 1990.

These carrier fluids are believed to act as a carrier for the fuel additive composition of the present invention and to assist in removing and retarding deposits. The carrier fluid may also exhibit synergistic deposit control properties when used in combination with the fuel additive composition of this invention.

The carrier fluids are typically employed in amounts ranging from about 25 to about 5000 ppm by weight of the hydrocarbon fuel, preferably from 100 to 3000 ppm of the fuel. Preferably, the ratio of carrier fluid to deposit control additive will range from about 0.2:1 to about 10:1, more preferably from 0.5:1 to 3:1.

When employed in a fuel concentrate, carrier fluids will generally be present in amounts ranging from about 20 to about 60 weight percent, preferably from 30 to 50 weight percent.

PREPARATIONS AND EXAMPLES

A further understanding of the invention can be had in the following nonlimiting Examples. Wherein unless expressly stated to the contrary, all temperatures and temperature ranges refer to the Centigrade system and the term "ambient" or "room temperature" refers to about 20° C.–25° C. The term "percent" or "%" refers to weight percent and the term "mole" or "moles" refers to gram moles. The term "equivalent" refers to a quantity of reagent equal in moles, to the moles of the preceding or succeeding reactant recited in that example in terms of finite moles or finite weight or volume. Where given, proton-magnetic resonance spectrum (p.m.r. or n.m.r.) were determined at 300 mHz, signals are assigned as singlets (s), broad singlets (bs), doublets (d), double doublets (dd), triplets (t), double triplets (dt), quartets (q), and multiplets (m), and cps refers to cycles per second.

Example 1

Preparation of Polyisobutyl Phenol

To a flask equipped with a magnetic stirrer, reflux condenser, thermometer, addition funnel and nitrogen inlet was added 203.2 grams of phenol. The phenol was warmed to 40° C. and the heat source was removed. Then, 73.5 milliliters of boron trifluoride etherate was added dropwise. 1040 grams of Ultravis 10 Polyisobutene (molecular weight 950, 76% methylvinylidene, available from British Petroleum) was dissolved in 1,863 milliliters of hexane. The polyisobutene was added to the reaction at a rate to maintain the temperature between 2220 C.–27° C. The reaction mixture was stirred for 16 hours at room temperature. Then, 400 milliliters of concentrated ammonium hydroxide was added, followed by 2,000 milliliters of hexane. The reaction mixture was washed with water (3×2,000 milliliters), dried over magnesium sulfate, filtered and the solvents removed under vacuum to yield 1,056.5 grams of a crude reaction product. The crude reaction product was determined to contain 80% of the desired product by proton NMR and chromatography on silica gel eluting with hexane, followed by hexane: ethylacetate: ethanol (93:5:2).

Example 2

Preparation of

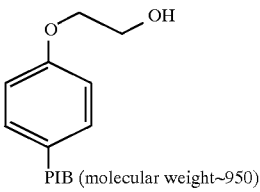

PIB (molecular weight~950)

Potassium hydride (1.1 grams of a 35 weight percent dispersion of in mineral oil) and 4-polyisobutyl phenol (99.7 grams, prepared as in example 1) were added to a flask equipped with a magnetic stirrer, reflux condenser, nitrogen inlet and thermometer. The reaction was heated at 130° C. for one hour and then cooled to 100° C. Ethylene carbonate (8.6 grams) was added and the mixture was heated at 160° C. for 16 hours. The reaction was cooled to room temperature and one milliliter of isopropanol was added. The reaction was diluted with one liter of hexane, washed three times with water and once with brine. The organic layer was dried over anhydrous magnesium sulfate, filtered and the solvents removed in vacuo to yield 98.0 grams of the desired product as a yellow oil.

Example 3

Preparation of

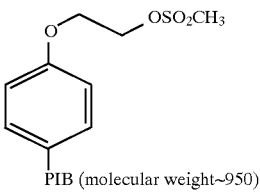

PIB (molecular weight~950)

The alcohol from Example 2 (20.0 grams), triethylamine (2.9 mL), and anhydrous dichloromethane (200 mL) were combined. The solution was cooled to 0° C. and methanesulfonyl chloride (1.5 mL) was added dropwise. The reaction was stirred at room temperture under nitrogen for 16 hours. The solution was diluted with dichloromethane (600 mL) and was washed twice with saturated aqueous sodium bicarbonate solution and once with brine. The organic layer was dried over anhydrous sodium sulfate, filtered and the solvents removed in vacuo to yield 20.4 grams as a yellow oil.

Example 4

Preparation of

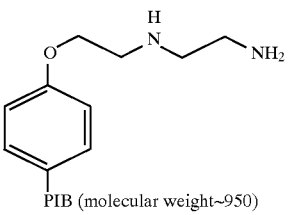

PIB (molecular weight~950)

Ethylenediamine (12.3 mL) and anhydrous toluene (100 mL) were combined under nitrogen. The product from Example 3 (20.4 grams, dissolved in 100 mL of anhydrous toluene) was added dropwise. The resulting solution was refluxed for 16 hours. The solution was diluted with hexane (600 mL) and was washed once with saturated aqueous sodium bicarbonate solution, three times with water and once with brine. The organic layer was dried over anhydrous sodium sulfate, filtered and the solvents removed in vacuo to yield 15.1 grams as a yellow oil. The oil was chromatographed on silica gel, eluting with hexane/diethyl ether (50:50) then hexane/diethyl ether/methanol/isopropylamine (40:40:15:5) to yield 10.3 grams of the desired product as a yellow oil. $^1$H NMR (CDCL$_3$) d 7.25 (d, 2H), 6.8 (d, 2H), 4.1 (t, 2H), 3.0 (t, 2H), 2.85 (t, 2H), 2.75 (t, 2H), 1.95 (bs, 3H), 1.5–0.7 (m, 137H).

Example 5

Preparation of

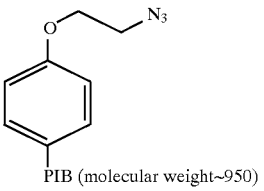

PIB (molecular weight~950)

A mesylate prepared as described in Example 3 (406.5 grams), sodium azide (198.2 grams), Adogen 464, a methyltrialkyl (C$_8$–C$_{10}$) ammonium chloride available from Ashland Chemical (8.0 mL), N,N-dimethyformamide (800 mL) and toluene (1.2 L) were combined. The reaction was refluxed for sixteen hours and cooled to room temperature. The mixture was filtered and the solvent was removed in vacuo. The residue was diluted with hexane (3.0 L) and washed three times with water and once with brine. The organic layer was dried over anhydrous magnesium sulfate, filtered and the solvents removed in vacuo to yield 334.3 grams of the desired azide as a yellow oil.

Example 6

Preparation of

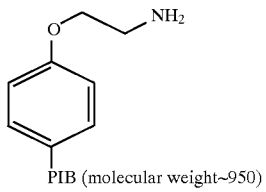

A solution of the product from Example 5 (334.3 grams) in ethyl acetate (750 mL) and toluene (750 mL), containing 10% palladium on charcoal (7.0 grams) was hydrogenolyzed at 35–40 psi for 16 hours on a Parr low pressure hydrogenator. Catalyst filtration and removal of the solvent in vacuo yielded 322.3 grams of the desired product as a yellow oil. $^1$H NMR (CDCl$_3$) d 7.25 (d, 2H), 6.8 (d, 2H), 4.0 (t, 1H), 3.1 (t, 2H), 2.35 (bs, 2H), 0.7–1.6 (m, 137H).

Example 7

Preparation of

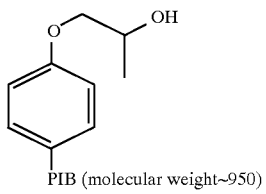

Potassium hydride (15.1 grams of a 35 weight percent dispersion of in mineral oil) and 4-polyisobutyl phenol (1378.5 grams, prepared as in Example 1) were added to a flask equipped with a mechanical stirrer, reflux condensor, nitrogen inlet and thermometer. The reaction was heated at 130° C. for one hour and then cooled to 100° C. Propylene carbonate (115.7 milliliters) was added and the mixture was heated at 160° C. for 16 hours. The reaction was cooled to room temperature and ten milliliters of isopropanol were added. The reaction was diluted with ten liters of hexane, washed three times with water and once with brine. The organic layer was dried over anhydrous magnesium sulfate, filtered and the solvents removed in vacuo to yield 1301.7 grams of the desired product as a yellow oil.

Example 8

Preparation of

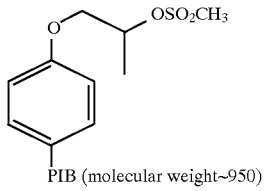

The alcohol from Example 7 (50.0 grams), triethylamine (7.0 mL), and anhydrous dichloromethane (500 mL) were combined. The solution was cooled to 0° C. and methanesulfonyl chloride (3.7 mL) was added dropwise. The reaction was stirred at room tempertaure under nitrogen for 16 hours. The solution was diluted with dichloromethane (1.5L) and was washed three times with saturated aqueous sodium bicarbonate solution and once with brine. The organic layer was dried over anhydrous sodium sulfate, filtered and the solvents removed in vacuo to yield 57.7 grams as a yellow oil.

Example 9

Preparation of

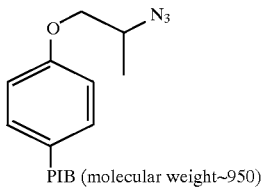

The mesylate from Example 8 (57.7 grams), sodium azide (27.1 grams), Adogen 464 (1.0 mL), N,N-dimethyformamide (400 mL) and toluene (600 mL) were combined. The reaction was refluxed for sixteen hours and cooled to room temperature. The mixture was filtered and the solvent was removed in vacuo. The residue was diluted with hexane (1.5L) and washed three times with water and once with brine. The organic layer was dried over anhydrous magnesium sulfate, filtered and the solvents removed in vacuo to yield 43.1 grams of the desired azide as a yellow oil.

Example 10

Preparation of

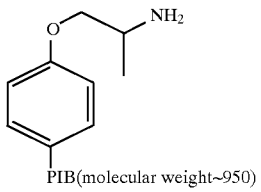

A solution of the product from Example 9 (43.1 grams) in ethyl acetate (100 mL) and toluene (100 mL), containing 10% palladium on charcoal (2.0 grams) was hydrogenolyzed at 35–40 psi for 16 hours on a Parr low pressure hydrogenator. Catalyst filtration and removal of the solvent in vacuo yielded 41.5 grams of the desired product as a yellow oil. $^1$H NMR (CDCl$_3$) d 7.25 (d, 2H), 6.85 (d, 2H), 3.9 (abq, 1H), 3.65 (abq, 1H), 3.35 (m, 1H), 1.9 (bs, 2H), 0.7–1.6 (m, 140H).

Example 11

Preparation of Dodecylphenoxy Poly(oxybutylene) poly(oxypropylene) Amine

A dodecylphenoxypoly(oxybutylene)poly(oxypropylene) amine was prepared by the reductive amination with ammonia of the random copolymer poly(oxyalkylene) alcohol, dodecylphenoxy poly(oxybutylene)poly(oxypropylene) alcohol, wherein the alcohol has an average molecular weight of about 1598. The poly(oxyalkylene) alcohol was prepared from dodecylphenol using a 75/25 weight/weight ratio of butylene oxide and propylene oxide, in accordance with the procedures described in U.S. Pat. Nos. 4,191,537; 2,782,240 and 2,841,479, as well as in Kirk-Othmer, "Encyclopedia of Chemical Technology", 4th edition, Volume 19, 1996, page 722. The reductive amination of the poly (oxyalkylene) alcohol was carried out using conventional techniques as described in U.S. Pat. Nos. 5,112,364; 4,609, 377 and 3,440,029.

Example 12

Single-Cylinder Engine Test

The test compounds were blended in gasoline and their deposit reducing capacity determined in an ASTM/CFR single-cylinder engine test.

A Waukesha CFR single-cylinder engine was used. Each run was carried out for 15 hours, at the end of which time the intake valve was removed, washed with hexane and weighed. The previously determined weight of the clean valve was subtracted from the weight of the valve at the end of the run. The differences between the two weights is the weight of the deposit. A lesser amount of deposit indicates a superior additive. The operating conditions of the test were as follows: water jacket temperature 200° F.; intake manifold vacuum of 12 in. Hg, air-fuel ratio of 12, ignition spark timing of 40° BTC; engine speed is 1800 rpm; the engine oil is a commercial SAE 30 grade.

The amount of carbonaceous deposit in milligrams on the intake valves is reported for each of the test compounds in Table I and Table II.

TABLE I

| Sample[1] | Intake Valve Deposit Weight (in milligrams) | | |
|---|---|---|---|
| | Run 1 | Run 2 | Average |
| Base Fuel | 333.5 | 354.9 | 344.2 |
| Example 4 | 22.5 | 22.7 | 22.6 |

[1]At 150 parts per million actives (ppma).

TABLE II

| Sample[1] | Intake Valve Deposit Weight (in milligrams) | | |
|---|---|---|---|
| | Run 1 | Run 2 | Average |
| Base Fuel | 323.8 | 312.1 | 318.0 |
| Example 6 | 12.1 | 21.0 | 16.6 |

[1]At 125 parts per million actives (ppma).

The base fuel employed in the above single-cylinder engine tests was a regular octane unleaded gasoline containing no fuel detergent. The test compounds were admixed with the base fuel to give the concentrations indicated in the tables.

The data in Table I and Table II illustrates the significant reduction in intake valve deposits provided by the polyalkylphenoxyaminoalkanes employed in the present invention (Examples 4 and 6) compared to the base fuel.

The combination of polyalkylphenoxyaminoalkane and poly(oxyalkylene) amine was also tested in the singlecylinder engine test and the amount of carbonaceous deposit in milligrams on the intake valves is reported in Table III.

TABLE III

| Sample | Conc. (ppma) | Intake Valve Deposit Weight (in milligrams) | | |
|---|---|---|---|---|
| | | Run 1 | Run 2 | Average |
| Base Fuel | — | 250.3 | 253.1 | 251.6 |
| Polyalkylphenoxy-aminoalkane/ Carrier Fluid[1] | 50/50 | 188 | 149.8 | 169 |
| Polyalkylphenoxy-aminoalkane/Poly (oxyalkylene) Amine[2] | 50/50 | 9.4 | 4.1 | 6.75 |
| Polyalkylphenoxy-aminoalkane/Poly (oxyalkylene) Amine[3] | 50/50 | 21.2 | 14.3 | 17.8 |
| Polyalkylphenoxy-aminoalkane/ Carrier Fluid[4] | 50/50 | 131.8 | 111.5 | 121.6 |
| Polyalkylphenoxy-aminoalkane/Poly (oxyalkylene) Amine[5] | 50/50 | 0 | 0 | 0 |
| Polyalkylphenoxy-aminoalkane/Poly (oxyalkylene) Amine[6] | 50/50 | 1 | 1.2 | 1.1 |

[1]Mixture of 50 ppma of polyisobutylphenoxyaminoalkane prepared as described in Example 10 and 50 ppm of a dodecylphenyl poly(oxybutylene) alcohol carrier fluid.
[2]Mixture of 50 ppma of polyisobutylphenoxyaminoalkane prepared as described in Example 10 and 50 ppma of dodecylphenoxypoly(oxybutylene) poly(oxypropylene) amine prepared as described in Example 11.
[3]Mixture of 50 ppma of polyisobutylphenoxyaminoalkane prepared as described in Example 10 and 50 ppma of a dodecylphenyl poly(oxybutylene) ethylene diamine carbamate (molecular weight about 1600), prepared essentially as described in Examples 6–8 of U.S. Pat. No. 4,197,537.
[4]Mixture of 50 ppma of polyisobutylphenoxyaminoalkane prepared as described in Example 6 and 50 ppm of a dodecylphenylpoly(oxybutylene) alcohol carrier fluid.
[5]Mixture of 50 ppma of polyisobutylphenoxyaminoalkane prepared as described in Example 6 and 50 ppma of dodecyclphenoxypoly(oxybutylene) poly(oxypropylene) amine prepared as described in Example 11.
[6]Mixture of 50 ppma of polyisobutylphenoxyaminoalkane prepared as described in Example 6 and 50 ppma of a dodecylphenyl poly(oxybutylene) ethylene diamine carbamate dodecylphenyl poly(oxybutylene) ethylene diamine carbamate (molecular weight about 1600), prepared essentially as described in Examples 6–8 of U.S. Pat. No. 4,197,537.

The data in Table III demonstrates that the combination of a polyalkylphenoxyaminoalkane and a poly(oxyalkylene) amine has a beneficial effect and gives significantly better intake valve deposit control than the polyalkylphenoxyaminoalkane component with a carrier fluid.

What is claimed is:

1. A fuel additive composition comprising:
   (a) a polyalkylphenoxyaminoalkane compound of the formula:

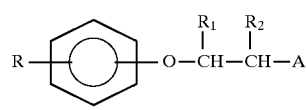

or a fuel-soluble salt thereof, wherein R is a polyalkyl group having an average molecular weight in the range of about 600 to 5,000;

$R_1$ and $R_2$ are independently hydrogen or lower alkyl having 1 to 6 carbon atoms; and A is amino, N-alkyl amino having about 1 to about 20 carbon atoms in the alkyl group, N,N-dialkyl amino having about 1 to about 20 carbon atoms in each alkyl group, or a polyamine moiety having about 2 to about 12 amine nitrogen atoms and about 2 to about 40 carbon atoms; and (b) a poly(oxyalkylene) amine having at least one basic nitrogen atom and a sufficient number of oxyalkylene units to render the poly(oxyalkylene) amine soluble in hydrocarbons boiling in the gasoline or diesel fuel range.

2. The fuel additive composition according to claim 1, wherein one of $R_1$ and $R_2$ is hydrogen or lower alkyl of 1 to 4 carbon atoms, and the other is hydrogen.

3. The fuel additive composition according to claim 2, wherein one of $R_1$ and $R_2$ is hydrogen, methyl or ethyl, and the other is hydrogen.

4. The fuel additive composition according to claim 3, wherein $R_2$ is hydrogen, methyl or ethyl, and $R_1$ is hydrogen.

5. The fuel additive composition according to claim 1, wherein R is a polyalkyl group having an average molecular weight in the range of about 600 to 3,000.

6. The fuel additive composition according to claim 5, wherein R is a polyalkyl group having an average molecular weight in the range of about 700 to 3,000.

7. The fuel additive composition according to claim 6, wherein R is a polyalkyl group having an average molecular weight in the range of about 900 to 2,500.

8. The fuel additive composition according to claim 1, wherein R is a polyalkyl group derived from polypropylene, polybutene, or a polyalphaolefin oligomer of 1-octene or 1-decene.

9. The fuel additive composition according to claim 8, wherein R is a polyalkyl group derived from polyisobutene.

10. The fuel additive composition according to claim 9, wherein the polyisobutene contains at least about 20% of a methylvinylidene isomer.

11. The fuel additive composition according to claim 1, wherein A is amino, N-alkyl amino or a polyamine moiety.

12. The fuel additive composition according to claim 11, wherein A is amino or N-alkyl amino having from about 1 to about 4 carbon atoms in the alkyl group.

13. The fuel additive composition according to claim 12, wherein A is amino.

14. The fuel additive composition according to claim 11, wherein A is a polyamine moiety having from about 2 to about 12 amine nitrogen atoms and from about 2 to about 40 carbon atoms.

15. The fuel additive composition according to claim 14, wherein A is a polyamine moiety derived from a polyalkylene polyamine containing from about 2 to about 12 amine nitrogen polyamine atoms and from about 2 to about 24 carbon atoms.

16. The fuel additive composition according to claim 15, wherein the polyalkylene polyamine has the formula:

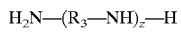

wherein $R_3$ is an alkylene group having from about 2 to about 6 carbon atoms and z is an integer from about 1 to about 4.

17. The fuel additive composition according to claim 16, wherein $R_3$ is an alkylene group having from about 2 to about 4 carbon atoms.

18. The fuel additive composition according to claim 17, wherein the polyalkylene polyamine is ethylene diamine or diethylene triamine.

19. The fuel additive composition according to claim 18, wherein the polyalkylene polyamine is ethylene diamine.

20. The fuel additive composition according to claim 1, wherein R is a polyalkyl group derived from polyisobutene, $R_1$ and $R_2$ are hydrogen and A is amino or a polyamine moiety derived from ethylene diamine.

21. The fuel additive composition according to claim 1, wherein said poly(oxyalkylene) amine has a molecular weight in the range of about 500 to about 10,000.

22. The fuel additive composition according to claim 1, wherein said poly(oxyalkylene) amine contains at least about 5 oxyalkylene units.

23. The fuel additive composition according to claim 1, wherein said poly(oxyalkylene) amine is a hydrocarbyl poly(oxyalkylene) polyamine.

24. The fuel additive composition according to claim 1, wherein said poly(oxyalkylene) amine is a hydrocarbyl poly(oxyalkylene) aminocarbamate.

25. The fuel additive composition according to claim 24, wherein the hydrocarbyl group of said hydrocarbyl poly (oxyalkylene) aminocarbamate contains from 1 to about 30 carbon atoms.

26. The fuel additive composition according to claim 25, wherein said hydrocarbyl group of said hydrocarbyl poly (oxyalkylene) aminocarbamate is an alkylphenyl group.

27. The fuel additive composition according to claim 26, wherein the alkyl moiety of said alkylphenyl group is tetrapropenyl.

28. The fuel additive composition according to claim 24, wherein the amine moiety of said hydrocarbyl poly (oxyalkylene) aminocarbamate is derived from a polyamine having from 2 to 12 amine nitrogen atoms and from 2 to 40 carbon atoms.

29. The fuel additive composition according to claim 28, wherein said polyamine is a polyalkylene polyamine having 2 to 12 amine nitrogen atoms and 2 to 24 carbon atoms.

30. The fuel additive composition according to claim 29, wherein said polyalkylene polyamine is selected from the group consisting of ethylenediamine, propylenediamine, diethylenetriamine and dipropylenetriamine.

31. The fuel additive composition according to claim 24, wherein the poly(oxyalkylene) moiety of said hydrocarbyl poly(oxyalkylene) aminocarbamate is derived from $C_2$ to $C_5$ oxyalkylene units.

32. The fuel additive composition according to claim 24, wherein said hydrocarbyl poly(oxyalkylene) aminocarbamate is an alkylphenyl poly(oxybutylene) aminocarbamate, wherein the amine moiety is derived from ethylenediamine or diethylenetriamine.

33. The fuel additive composition according to claim 1, wherein said poly(oxyalkylene) amine is a hydrocarbyl poly(oxyalkylene) monoamine.

34. The fuel additive composition according to claim 33, wherein said hydrocarbyl poly(oxyalkylene) monoamine is an alkylphenyl poly(oxyalkylene) monoamine, wherein the poly(oxyalkylene) moiety contains oxypropylene units or oxybutylene units or mixtures thereof.

35. The fuel additive composition according to claim 34, wherein the alkylphenyl group is tetrapropenylphenyl.

36. A fuel composition comprising a major amount of hydrocarbons boiling in the gasoline or diesel range and an effective deposit-controlling amount of a fuel additive composition comprising:

(a) a polyalkylphenoxyaminoalkane compound of the formula:

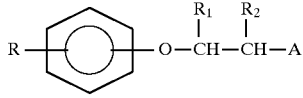

or a fuel-soluble salt thereof, wherein R is a polyalkyl group having an average molecular weight in the range of about 600 to 5,000;

$R_1$ and $R_2$ are independently hydrogen or lower alkyl having 1 to 6 carbon atoms; and A is amino, N-alkyl amino having about 1 to about 20 carbon atoms in the alkyl group, N,N-dialkyl amino having about 1 to about 20 carbon atoms in each alkyl group, or a polyamine moiety having about 2 to about 12 amine nitrogen atoms and about 2 to about 40 carbon atoms; and (b) a poly(oxyalkylene) amine having at least one basic nitrogen atom and a sufficient number of oxyalkylene units to render the poly(oxyalkylene) amine soluble in hydrocarbons boiling in the gasoline or diesel fuel range.

37. The fuel composition according to claim 36, wherein one of $R_1$ and $R_2$ is hydrogen or lower alkyl of 1 to 4 carbon atoms, and the other is hydrogen.

38. The fuel composition according to claim 37, wherein $R_2$ is hydrogen, methyl or ethyl, and $R_1$ is hydrogen.

39. The fuel composition according to claim 36, wherein R is a polyalkyl group having an average molecular weight in the range of about 700 to 3,000.

40. The fuel composition according to claim 36, wherein R is a polyalkyl group derived from polypropylene, polybutene, or a polyalphaolefin oligomer of 1-octene or 1-decene.

41. The fuel composition according to claim 40, wherein R is a polyalkyl group derived from polyisobutene.

42. The fuel composition according to claim 36, wherein A is amino, N-alkyl amino or a polyamine moiety.

43. The fuel composition according to claim 42, wherein A is amino.

44. The fuel composition according to claim 42, wherein A is a polyamine moiety derived from a polyalkylene polyamine containing from about 2 to about 12 amine nitrogen polyamine atoms and from about 2 to about 24 carbon atoms.

45. The fuel composition according to claim 44, wherein the polyalkylene polyamine has the formula:

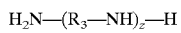

wherein $R_3$ is an alkylene group having from about 2 to about 6 carbon atoms and z is an integer from about 1 to about 4.

46. The fuel composition according to claim 45, wherein the polyalkylene polyamine is ethylene diamine or diethylene triamine.

47. The fuel composition according to claim 36, wherein R is a polyalkyl group derived from polyisobutene, $R_1$, and $R_2$ are hydrogen and A is amino or a polyamine moiety derived from ethylene diamine.

48. The fuel composition according to claim 36, wherein said poly(oxyalkylene) amine is a hydrocarbyl poly (oxyalkylene) aminocarbamate.

49. The fuel composition according to claim 48, wherein the hydrocarbyl group of said hydrocarbyl poly (oxyalkylene) aminocarbamate contains from 1 to about 30 carbon atoms; and wherein the amine moiety of said hydrocarbyl poly(oxyalkylene) aminocarbamate is derived from a polyamine having from 2 to 12 amine nitrogen atoms and from 2 to 40 carbon atoms.

50. The fuel composition according to claim 49, wherein said hydrocarbyl group of said hydrocarbyl poly (oxyalkylene) aminocarbamate is an alkylphenyl group; and wherein said polyalkylene polyamine is selected from the group consisting of ethylenediamine, propylenediamine, diethylenetriamine and dipropylenetriamine.

51. The fuel composition according to claim 50, wherein the alkyl moiety of said alkylphenyl group is tetrapropenyl.

52. The fuel composition according to claim 48, wherein said hydrocarbyl poly(oxyalkylene) aminocarbamate is an alkylphenyl poly(oxybutylene) aminocarbamate, wherein the amine moiety is derived from ethylenediamine or diethylenetriamine.

53. The fuel composition according to claim 36, wherein said poly(oxyalkylene) amine is a hydrocarbyl poly (oxyalkylene) monoamine.

54. The fuel composition according to claim 53, wherein said hydrocarbyl poly(oxyalkylene) monoamine is an alkylphenyl poly(oxyalkylene) monoamine, wherein the poly (oxyalkylene) moiety contains oxypropylene units or oxybutylene units or mixtures thereof.

55. The fuel composition according to claim 54, wherein the alkylphenyl group is tetrapropenylphenyl.

56. The fuel composition according to claim 36, wherein the composition contains from about 25 to about 2,000 parts per million by weight of said polyalkylphenoxyaminoalkane compound and about 25 to about 2,000 parts per million of said poly(oxyalkylene) amine.

57. The fuel composition according to claim 36, where the composition further contains from about 25 to about 5,000 parts per million by weight of a fuel-soluble, nonvolatile carrier fluid.

58. A fuel concentrate comprising an inert stable oleophilic organic solvent boiling in the range of from about 150° F. to 400° F. and from about 10 to about 70 weight percent of a fuel additive composition comprising:

(a) a polyalkylphenoxyaminoalkane compound of the formula:

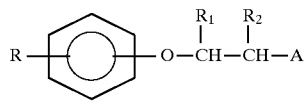

or a fuel-soluble salt thereof, wherein R is a polyalkyl group having an average molecular weight in the range of about 600 to 5,000;

$R_1$ and $R_2$ are independently hydrogen or lower alkyl having 1 to 6 carbon atoms; and A is amino, N-alkyl amino having about 1 to about 20 carbon atoms in the alkyl group, N,N-dialkyl amino having about 1 to about 20 carbon atoms in each alkyl group, or a polyamine moiety having about 2 to about 12 amine nitrogen atoms and about 2 to about 40 carbon atoms; and (b) a poly(oxyalkylene) amine having at least one basic nitrogen atom and a sufficient number of oxyalkylene units to render the poly(oxyalkylene) amine soluble in hydrocarbons boiling in the gasoline or diesel fuel range.

59. The fuel concentrate according to claim 58, wherein one of $R_1$ and $R_2$ is hydrogen or lower alkyl of 1 to 4 carbon atoms, and the other is hydrogen.

60. The fuel concentrate according to claim 59, wherein $R_2$ is hydrogen, methyl or ethyl, and $R_1$ is hydrogen.

61. The fuel concentrate according to claim 58, wherein R is a polyalkyl group having an average molecular weight in the range of about 700 to 3,000.

62. The fuel concentrate according to claim 58, wherein R is a polyalkyl group derived from polypropylene, polybutene, or a polyalphaolefin oligomer of 1-octene or 1-decene.

63. The fuel concentrate according to claim 62, wherein R is a polyalkyl group derived from polyisobutene.

64. The fuel concentrate according to claim 58, wherein A is amino, N-alkyl amino or a polyamine moiety.

65. The fuel concentrate according to claim 64, wherein A is amino.

66. The fuel concentrate according to claim 64, wherein A is a polyamine moiety derived from a polyalkylene polyamine containing from about 2 to about 12 amine nitrogen polyamine atoms and from about 2 to about 24 carbon atoms.

67. The fuel concentrate according to claim 66, wherein the polyalkylene polyamine has the formula:

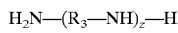

$$H_2N-(R_3-NH)_z-H$$

wherein $R_3$ is an alkylene group having from about 2 to about 6 carbon atoms and z is an integer from about 1 to about 4.

68. The fuel concentrate according to claim 67, wherein the polyalkylene polyamine is ethylene diamine or diethylene triamine.

69. The fuel concentrate according to claim 58, wherein R is a polyalkyl group derived from polyisobutene, $R_1$ and $R_2$ are hydrogen and A is amino or a polyamine moiety derived from ethylene diamine.

70. The fuel concentrate according to claim 58, wherein the fuel concentrate further contains from about 20 to about 60 weight percent of a fuel-soluble, nonvolatile carrier fluid.

71. The fuel concentrate according to claim 58, wherein said poly(oxyalkylene) amine is a hydrocarbyl poly(oxyalkylene) aminocarbamate.

72. The fuel concentrate according to claim 71, wherein the hydrocarbyl group of said hydrocarbyl poly(oxyalkylene) aminocarbamate contains from 1 to about 30 carbon atoms; and wherein the amine moiety of said hydrocarbyl poly(oxyalkylene) aminocarbamate is derived from a polyamine having from 2 to 12 amine nitrogen atoms and from 2 to 40 carbon atoms.

73. The fuel concentrate according to claim 72, wherein said hydrocarbyl group of said hydrocarbyl poly(oxyalkylene) aminocarbamate is an alkylphenyl group; and wherein said polyalkylene polyamine is selected from the group consisting of ethylenediamine, propylenediamine, diethylenetriamine and dipropylenetriamine.

74. The fuel concentrate according to claim 73, wherein the alkyl moiety of said alkylphenyl group is tetrapropenyl.

75. The fuel concentrate according to claim 71, wherein said hydrocarbyl poly(oxyalkylene) aminocarbamate is an alkylphenyl poly(oxybutylene) aminocarbamate, wherein the amine moiety is derived from ethylenediamine or diethylenetriamine.

76. The fuel concentrate according to claim 58, wherein said poly(oxyalkylene) amine is a hydrocarbyl poly(oxyalkylene) monoamine.

77. The fuel concentrate according to claim 76, wherein said hydrocarbyl poly(oxyalkylene) monoamine is an alkylphenyl poly(oxyalkylene) monoamine, wherein the poly(oxyalkylene) moiety contains oxypropylene units or oxybutylene units or mixtures thereof.

78. The fuel concentrate according to claim 77, wherein the alkylphenyl group is tetrapropenylphenyl.

* * * * *